US008624741B2

(12) United States Patent
Batchelder et al.

(10) Patent No.: US 8,624,741 B2
(45) Date of Patent: Jan. 7, 2014

(54) PULSE OXIMETER ALARM SIMULATOR AND TRAINING TOOL

(75) Inventors: Keith Batchelder, New York, NY (US); Steve Allen, Longmont, CO (US); Roger Mecca, Corona Del Mar, CA (US)

(73) Assignee: Covidien LP, Mansfield, MA (US)

( * ) Notice: Subject to any disclaimer, the term of this patent is extended or adjusted under 35 U.S.C. 154(b) by 390 days.

(21) Appl. No.: 13/036,748

(22) Filed: Feb. 28, 2011

(65) Prior Publication Data

US 2012/0218111 A1    Aug. 30, 2012

(51) Int. Cl.
    *G08B 23/00*    (2006.01)
(52) U.S. Cl.
    USPC .................. 340/573.1; 600/323; 600/324
(58) Field of Classification Search
    USPC ........ 340/573.1; 600/323, 324, 483, 484, 529
    See application file for complete search history.

(56) References Cited

U.S. PATENT DOCUMENTS

| 5,865,736 | A | 2/1999 | Baker, Jr. |
| 6,078,898 | A | 6/2000 | Davis |
| 6,754,516 | B2 | 6/2004 | Mannheimer |
| 7,123,950 | B2 | 10/2006 | Mannheimer |
| 7,129,836 | B2 | 10/2006 | Lawson |
| 7,398,115 | B2 * | 7/2008 | Lynn .............................. 600/324 |
| 7,774,060 | B2 | 8/2010 | Westenskow |
| 2005/0247311 | A1 | 11/2005 | Vacchiano |
| 2007/0221225 | A1 | 9/2007 | Kutt |
| 2008/0059249 | A1 | 3/2008 | Joao |
| 2008/0059250 | A1 | 3/2008 | Joao |
| 2008/0081963 | A1 | 4/2008 | Naghavi |
| 2008/0091089 | A1 | 4/2008 | Guillory |
| 2008/0091090 | A1 | 4/2008 | Guillory |
| 2008/0287756 | A1 * | 11/2008 | Lynn .............................. 600/323 |
| 2010/0113909 | A1 | 5/2010 | Batchelder |
| 2011/0001605 | A1 * | 1/2011 | Kiani et al. .................... 340/5.6 |

FOREIGN PATENT DOCUMENTS

| GB | 2448323 | A | 10/2008 |
| JP | 2237544 | | 9/1990 |
| JP | 8256996 | | 10/1996 |
| WO | 2006109072 | A2 | 10/2006 |
| WO | 2007141246 | A3 | 12/2007 |
| WO | 2008075288 | A2 | 6/2008 |

OTHER PUBLICATIONS

Barnum, P.T., et al.; "Novel Pulse Oximetry Technology Capable of Reliable Bradycardia Monitoring in the Neonate," Respiratory Care, vol. 42, No. 1, p. 1072 (Nov. 1997).

Rheineck-Leyssius, Aart t., et al.; "Advanced Pulse Oximeter Signal Processing Technology Compared to Simple Averaging: I. Effect on Frequency of Alarms in the Operating Room," Journal of clinical Anestesia, vol. 11, pp. 192-195 (1999).

(Continued)

*Primary Examiner* — John A Tweel, Jr.

(57) ABSTRACT

According to various embodiments, methods and systems are provided herein for training a user in alarm behaviors of a medical device. The alarm behaviors may be accessed via a simulator system that obtains input regarding alarm settings, accesses stored plethysmographic waveform data representative of data obtained through the simulated medical device and that applies the alarm setting inputs to the stored plethysmographic waveform data to provide simulated alarm outputs representative of alarm outputs of the medical device.

20 Claims, 8 Drawing Sheets

(56) References Cited

OTHER PUBLICATIONS

Nilsson, Lena, et al.; "Monitoring of Respiratory Rate in Postoperative Care Using a New Photoplethysmographic Technique," Journal of Clinical Monitoring and Computing, vol. 16, pp. 309-315 (2000).

Belal, Suliman Yousef, et al.; "A fuzzy system for detecting distorted plethysmogram pulses in neonates and paediatric patients," Physiol. Meas., vol. 22, pp. 397-412 (2001).

Lutter, Norbert O., et al.; "False Alarm Rates of Three Third-Generation Pulse Oximeters in PACU, ICU and IABP Patients," Anesth Analg, vol. 94, pp. S69-S75 (2002).

Yoon, Gilwon, et al.; Multiple diagnosis based on Photoplethysmography: hematocrit, SpO2, pulse and respiration, Optics in Health Care and Biomedical optics: Diagnostics and Treatment; Proceedings of the SPIE, vol. 4916; pp. 185-188 (2002).

Neumann, R., et al.; "Fourier Artifact suppression Technology Provides Reliable SpO2,," Abstracts, A11, p. S105. (undated), Nov. 29, 2011.

* cited by examiner

PULSE OXIMETER ALARM SIMULATOR AND TRAINING TOOL

BACKGROUND

The present disclosure relates generally to systems and methods for providing instruction and training for medical devices. More particularly, the disclosure provides instruction and training around alarm behavior in medical devices having alarm management systems.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of healthcare, caregivers (e.g., doctors and other healthcare professionals) often desire to monitor certain physiological characteristics of their patients. Accordingly, a wide variety of monitoring devices have been developed for monitoring many such physiological characteristics. These monitoring devices often provide doctors and other healthcare personnel with information that facilitates provision of the best possible healthcare for their patients. As a result, such monitoring devices have become a perennial feature of modern medicine.

One technique for monitoring physiological characteristics of a patient is commonly referred to as pulse oximetry, and the devices built based upon pulse oximetry techniques are commonly referred to as pulse oximeters. Pulse oximeters may be used to measure and monitor various blood flow characteristics of a patient. For example, a pulse oximeter may be utilized to monitor the blood oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time-varying amount of arterial blood in the tissue during each cardiac cycle.

Pulse oximetry monitors have become increasingly complex, providing a variety of settings that are configurable by the end user. For example, the settings that trigger an alarm indication may be selected based on the patient's clinical condition. In particular, the alarm settings used for a relatively healthy and active patient may have a higher threshold for certain types of alarms, while a patient in a critical care setting may have alarm settings that include lower thresholds. Configuring a monitor with improper threshold settings may cause an alarm to be too sensitive and result in nuisance alarms.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

Figure 1:
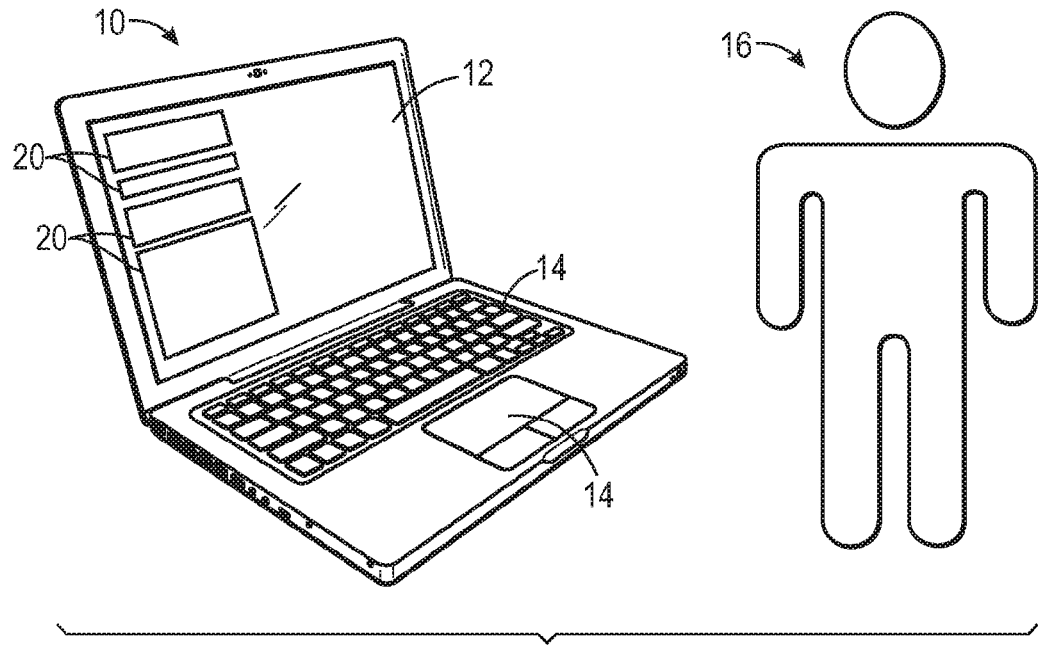
FIG. 1 is an example of a simulator system in accordance with embodiments.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Provided herein are systems and methods for simulating alarm conditions in a medical monitor. These systems for generating simulated alarm conditions may be used in conjunction with an interactive training tool for end users of the medical monitor. As medical devices become increasingly sophisticated and customizable, it is desirable to have a variety of methods of training and instruction for the healthcare professionals who will take advantage of the customizations. In particular, interactive alarm simulators allow caregivers to change alarm settings and experience the relative changes in alarm sensitivity between various alarm settings for a particular patient. The alarm simulators and training tools as provided may also allow caregivers to experience the effect of alarm settings on different types of patients, e.g., patients with a particular clinical profile. Further, caregivers may use the training tool to become more familiar with the alarm settings and alarm acknowledgement tools of the monitor. As provided, the alarm simulators and alarm configuration training tools may be used in lieu of or in conjunction with passive instruction techniques, such video demonstrations, textual based instruction, and demonstration modes on the medical monitor.

Medical device alarms may exhibit a wide range of behaviors based upon physiological conditions as well as settings input by the healthcare professionals and students configuring the machines. For example, a pulse oximetry monitor such as those available from Nellcor Puritan Bennet LLC, may incorporate a SatSeconds™ alarm management system. Generally speaking, SatSeconds™ alarm management operates by integrating an area between an alarm threshold and a patient's measured physiological parameters over time. For example, rather than sounding an alarm as soon as the patient's measured SpO$_2$ drops below a threshold value, the SatSeconds™ system measures an area by integrating the difference between a threshold SpO$_2$ and the patient's SpO$_2$ level when the patient's SpO$_2$ level is below the threshold. When the SatSeconds™ value exceeds a threshold value (e.g., a preset threshold or a user-input threshold), the caregiver may be alerted that the patient's oxygen saturation is too low. A healthcare professional may determine the appropriate SpO$_2$ threshold limits as well as the appropriate SatSeconds™ threshold limits, in a SatSeconds™ alarm management system. Setting improper SatSeconds™ thresholds may cause the alarm system to be too sensitive, which may increase an incidence of nuisance alarms.

Additionally, a pulse oximetry monitor or other medical device as provided herein may incorporate saturation pattern detection (SPD). Generally speaking, saturation pattern detection is based on an SPD index (SPDi) created by analyzing SpO$_2$ values from the monitor. When the SPDi crosses a threshold, an alarm is triggered. SPD alarms may include a tolerance level input that allows a healthcare professional to select a level of tolerance or sensitivity. For example, in some embodiments, a SPD threshold may be set at 1, 2, or 3 representing a high, medium, and low threshold, respectively. The SPD threshold settings may affect a monitor in multiple ways, e.g., the threshold may determine how certain alarms on the medical device will respond. For example, SPD may be represented by a hollow triangular symbol on the display of a medical device. As the events associated with the alarm, the SPDi values, begin to near the set SPD threshold, the triangular shape may start to fill, to indicate that an SPD threshold is nearing. Additionally, as the threshold is met, an SPD alarm may be triggered. Varying the SPD threshold may provide a wide range of alarm behaviors. As provided herein, the systems and devices may simulate the effects of various SPD settings to facilitate selecting the proper SPD threshold for a particular patient.

In certain embodiments, the systems and devices provided herein may be employed to instruct healthcare professionals and students regarding the settings of alarm management systems, such as the SatSeconds™ and SPD alarm management systems. The present techniques may include providing a simulator system for a medical device that will simulate alarm behaviors based upon medical device configuration settings, simulated external stimuli, and/or simulated physiological data provided to the simulator system. Additionally, the simulator system may have a user assessment module that tests the user's ability to i) correctly configure the machines, ii) provide diagnosis based on the machine outputs, and/or iii) provide intervention suggestions based upon the diagnosis.

With the foregoing in mind, FIG. 1 is an illustration of a simulator system 10, which may include a personal desktop computer, laptop computer, handheld device, etc. The simulator system 10 includes a display 12 and user inputs 14, which may include a mouse, track pad, keyboard, touch screen, etc. The simulator system 10 may provide a simulator user 16, such as a teacher, student, doctor, nurse, or medical technician, with graphical outputs 20. As will be discussed in more detail below, the graphical outputs 20 may include various graphical user interfaces representative of the medical device that is being simulated. In certain embodiments system 10 may be part of a pulse oximetry monitor or other medical device. In such embodiments, the system 10 may be accessible via a training menu or demo setting of the pulse oximetry monitor or other medical device and may provide default alarm settings illustrating how the alarms are affected by sensor reading inputs for the particular pulse oximetry monitor or other medical device.

Figure 2:
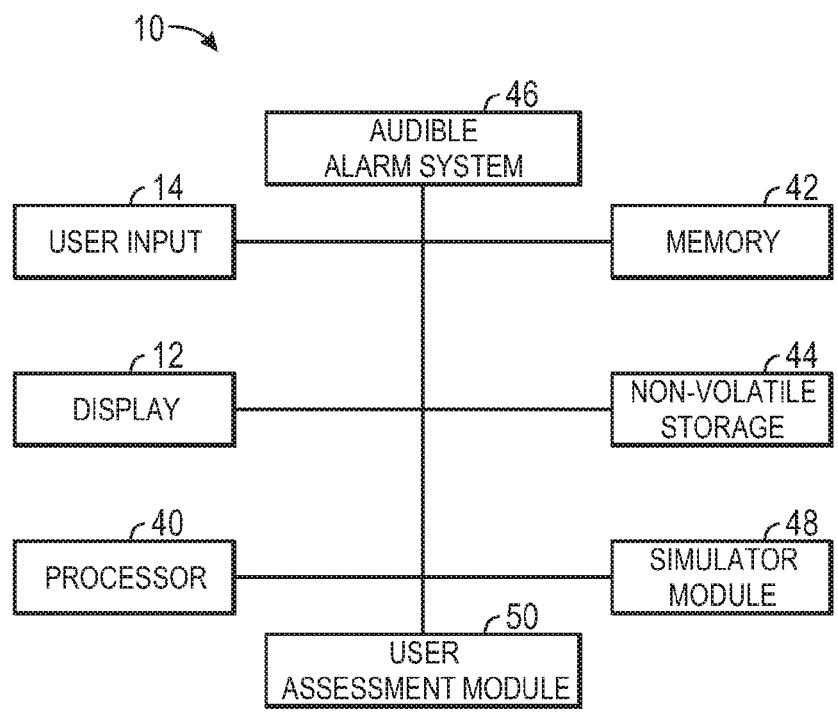
FIG. 2 is a block diagram of a simulator system in accordance with embodiments.

As depicted in FIG. 2, the simulator system 10 may include, among other things, a display 12, user inputs 14, one or more processors 40, memory 42, non-volatile storage 44, an audible alarm system 46, a simulator module 48, and a user assessment module 50. The various functional blocks shown in FIG. 2 may include hardware elements (including circuitry), software elements (including computer code stored on a computer-readable medium) or a combination of both hardware and software elements. Further, FIG. 2 is only one example of a particular implementation and is merely intended to illustrate the types of components that may be present in the simulator system. Based at least in part upon the plethysmographic waveform data (e.g., stored data), the processor 40 may calculate the oxygen saturation and/or heart rate using various algorithms, such as those employed by the Nellcor™ N-600x™ pulse oximetry monitor. These algorithms may employ certain coefficients, which may be stored in the memory 42 or other suitable computer-readable storage medium and accessed and operated according to processor 40 instructions.

In one implementation, the simulator module 48 and the user assessment module 50 in accordance with the present discussion may be developed and implemented using open source tools. Such a system may be developed as a web-based application, allowing distributed access or use of the application. For example, such an implementation may be developed using one or more of Java, Java server pages (JSP), structured query language (SQL), extensible markup language (XML), XML user interface language (XUL) and/or scalable vector graphics (SVG) technologies. In an alternate implementation, the simulator module may include instructions that may be executed by the processor 40, and stored on a non-volatile storage media 44, such as a CD-ROM or hard drive. In some instances, the non-volatile storage media 44 may be distributed in a bundle with a medical device the simulator system 10 simulates. The simulator module 48 is responsible for receiving inputs and deriving outputs representative of the medical device being simulated.

Further, the stored plethysmographic waveform data may comprise various forms including: a formatted text file, exported data from a medical device, a data file from a trend data creation utility, etc. The stored plethysmographic waveform data may be stored on the non-volatile storage media 44, or may be downloaded from an outside source through a network connection. In some embodiments, the simulator system 10 may intake the stored plethysmographic waveform data through an import screen, requesting the location of a simulated trend data file. In alternative embodiments, the simulator system 10 may select a data file from a plurality of stored data files based upon a user selection of physiological conditions, e.g. conditions listed in the import screen of the simulator system. For example, the simulator user 16 may desire to simulate the conditions of pulmonary edema to understand alarm behaviors for a patient with that condition. The user may select pulmonary edema from the list of physiological conditions, and the simulator system will import a simulated data file corresponding to that condition. In addition, a user may associate a physiological condition (e.g. pulmonary edema) with a particular set of stored plethysmographic waveform view. That is, the stored data may be associated with a patient diagnosis or with a particular clinical condition.

As an alternative to accessing stored plethysmographic waveform data, the plethysmographic waveform data may be at least in part user-created. The simulator system 10 may include a data creation module that allows a user to plot or draw simulation data. For example, the data creation module may provide a blank trend view window, which may allow a user to input plot or draw points representing points of representative physiological measurements. For example, a user might plot multiple $SpO_2$ measurements along a multitude of time positions. Upon entry of all of the measurement points, the data creation module may create a trend line, linking each of the plot points together. Alternatively, the data creation module may simply allow a user to draw a trend line, in the trend view window, without plotting individual measurements. This feature may allow a user to experience alarm settings for a simulated data set that may be relatively exaggerated for training purposes. For example, a user-created data plot may include oxygen saturation values that may be physiologically unlikely for an actual patient but that may be useful for showing the effects of certain alarm limits in extreme cases. In one embodiment, the user may save the simulated views.

Figure 3:
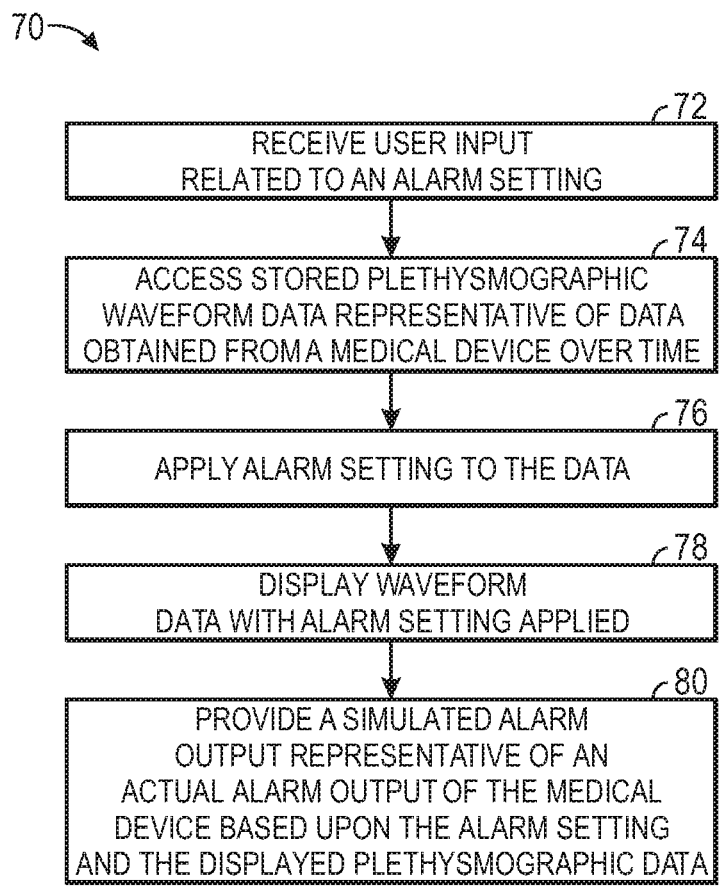
FIG. 3 is a flowchart depicting a simulation method in accordance with embodiments.

An example of a simulation method 70 is illustrated in the flowchart depicted in FIG. 3. The method 70 may be performed as an automated procedure by a system, such as a system 10 that includes display 12 and user inputs 14. In addition, certain steps of the method may be performed by a processor 40, or a processor-based device that may be part of the system 10 that includes instructions for implementing certain steps of the method 70. The simulation method 70 begins at block 72 when the simulator module 48 receives a user input related to an alarm setting. As will be discussed in more detail below, the alarm setting inputs may generally be obtained through an alarm settings configuration menu that is representative of an alarm settings configuration menu of the medical device in question.

At block 74, the simulator module 48 accesses stored plethysmographic waveform data representative of data obtained from the medical device over a period of time. For example, the stored plethysmographic waveform data may be representative of data acquired by a pulse oximetry sensor over a period of time that may be used to determine physiological parameters such as $SpO_2$ levels. Furthermore, the stored plethysmographic waveform data may be of the type used to determine pulse rate, respiration rate based on central drive, SPD index, expired $CO_2$, respiration rate based on airflow, and/or photopleth. In particular embodiments, the stored plethysmographic waveform data may be historical data acquired from one or more patients. In addition, the stored plethysmographic waveform data may be raw data, e.g. representative of data provided by a detector of a pulse oximetry sensor, or may be processed data that has undergone conditioning that may improve the signal to noise ratio. Alternatively, the stored plethysmographic waveform data may be in the form of calculated oxygen saturation or any suitable physiological parameter over time. In addition, the data may be synthetic data that has been specifically generated and tailored to the simulator module 48. The stored plethysmographic waveform data may include both simulated real-time sensor readings as well as instructions interpretable by the simulator module 48 as to how alarm settings should be applied to the stored plethysmographic waveform data. Alternatively, the stored plethysmographic waveform data may include pre-calculated alarm indicator values, e.g., an SPD index or integrated SatSeconds™ value for specific threshold values.

In block 76, the simulator module 48 applies the alarm setting inputs received in block 72 to the stored plethysmographic waveform data accessed in step 74. To apply the alarm settings, the stored plethysmographic waveform data may provide instructions to the simulator module 48 for application of the alarm setting inputs to the data as appropriate. For example, the system 10 may execute instructions to calculate alarm trigger points based upon the alarm setting input and the plethysmographic waveform data. For example, the alarm settings may be triggered based on the SatSeconds™ alarm management system as provided in U.S. Pat. No. 5,865,736; U.S. Pat. No. 6,754,516; and U.S. Pat. No. 7,123,950 or the SPD alarm management system as provided in U.S. Patent Publication No. 2010/0113909 to Batchelder et al., the specifications of both of which are incorporated by reference in their entirety herein for all purposes. In particular, the system 10 may calculate a physiological parameter from the data and determine if the calculated physiological parameter exceeds certain thresholds associated with alarm events. Applying the alarm settings may involve applying the thresholds and/or triggers to the calculated physiological parameters, which may represent a given time period.

After the simulator system applies the alarm setting inputs to the stored plethysmographic waveform data, the simulator system displays an output representative of a display of the medical device based on the plethysmographic waveform data with the alarm settings applied, in block 78. In certain embodiments, displaying the stored plethysmographic waveform data may include providing a trend view of the stored plethysmographic waveform data over time and providing alarm indicators at points in time when an alarm would trigger in the simulated medical device configured with the alarm setting inputs. In addition, in block 80, a simulated alarm output, representative of an actual alarm output of the medical device being simulated, may be provided to the simulator user, based upon the alarm settings and the stored plethysmographic waveform data. The alarm output may include visual alarms and/or audible alarms representative of alarms displayed on the medical device being simulated.

Figure 4:
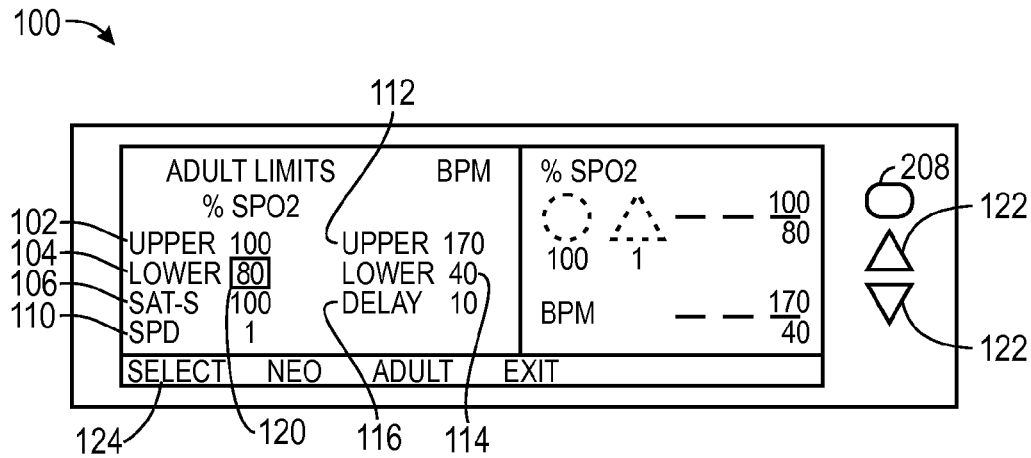
FIG. 4 depicts a simulated alarm settings configuration menu in which the lower $SpO_2$ limit has been selected.
Figure 5:
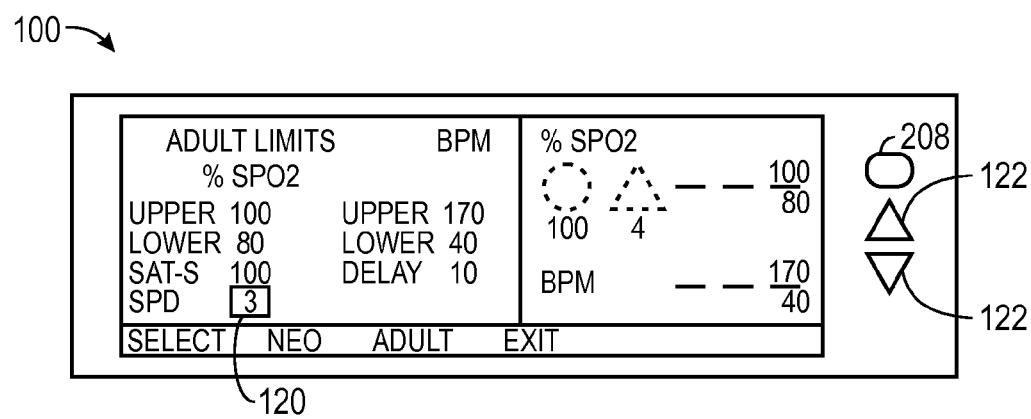
FIG. 5 depicts the simulated alarm settings configuration menu of FIG. 4 in which the saturation pattern detection alarm threshold has been selected.
Figure 6:
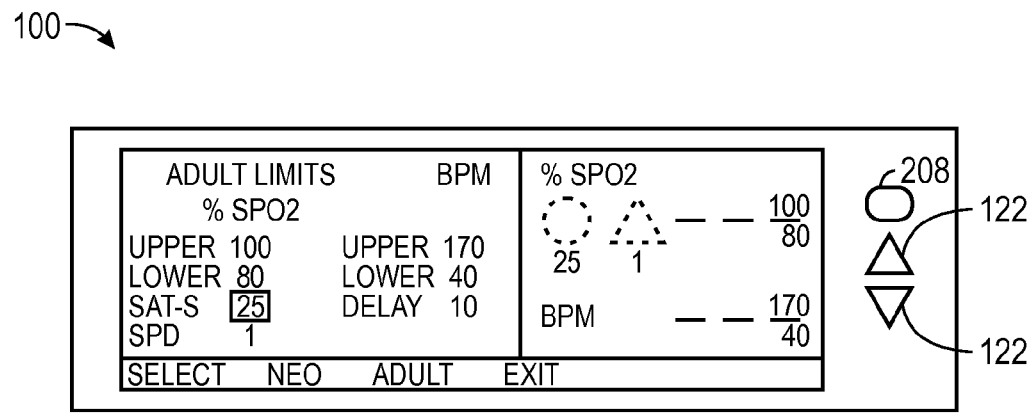
FIG. 6 depicts the simulated alarm settings configuration menu of FIG. 4 in which the SatSeconds™ alarm threshold has been selected.

In particular, the system 10 may facilitate understanding of the effect of various alarm settings on a medical device. To that end, the system 10 may provide one or more user input screens that are representative of the alarm configuration menus for the device in question. The user may manipulate one or more alarm settings and experience the differences between the settings as they are applied to the patient data. FIGS. 4-6 illustrate examples of alarm settings configuration menus 100 for a pulse oximetry monitor. The alarm settings configuration menu 100 provides one example of how alarm input settings may be obtained from the simulator user 16. In the illustrated embodiments, the pulse oximetry monitor includes settings for upper $SpO_2$ percentage limits 102 and lower $SpO_2$ percentage limits 104, a threshold value selector for oxygen saturation related alarms 106 (e.g., a SatSeconds™ alarm), a sensitivity value selector for SPD alarms 110, as well as upper 112, lower 114, and delay 116 thresholds for a heart rate alarm. The selection indicator box 120 illustrates the setting that may be changed. To change a setting, the simulator user 16 uses the toggle arrows 122 to navigate the selection indicator box 120 to the desired setting to be changed and then choosing the select option 124. It is envisioned that, in one embodiment, the user input is representative of the user input during operation of the device in question. As shown in FIG. 4, the selection indicator box 120 surrounds the lower SpO$_2$ percentage limit 104. After choosing the select option 124, the simulator user 16 may adjust the lower SpO$_2$ percentage limit 104 by selecting the toggle arrows 122. Adjusting the upper 102 and lower 104 thresholds provides the upper and lower bounds that determine where the SatSeconds™ alarm should begin integrating an alarm threshold. For example, in FIG. 4, the upper threshold 102 is at 100% and the lower threshold 104 is at 80%. Any time the sensor readings from the stored plethysmographic waveform rises above the upper threshold (e.g., 100%) or drops below the lower threshold (e.g., 80%), the simulator module 48 begins to integrate a SatSeconds™ value progressing towards the SatSeconds™ threshold.

As shown in FIG. 5, the simulator user 16 may navigate the selection indicator box 120 to select an SPD sensitivity setting 110. The SPD sensitivity setting 110 may include an integer setting, providing various threshold levels for the SPD alarm. For example, the SPD alarm may include four sensitivity or tolerance settings: Off, Low, Medium, and High represented by 0-3, respectively. In high sensitivity mode, the SPD threshold may be reduced, creating an increased potential for an SPD index to breach the SPD threshold, and thus trigger an SPD alarm. As shown in FIG. 5, the simulator user 16 may increase the SPD sensitivity setting 110 to 3, thus increasing the sensitivity of the SPD alarm and causing the SPD alarm to become more sensitive.

In FIG. 6, the simulator user 16 may adjust the threshold value selector for the oxygen saturation detection alarm 106. A decrease in the selected threshold value selector for the oxygen saturation detection alarm 106 may result in a more sensitive oxygen saturation detection alarm. For example, in FIG. 6, the oxygen saturation detection alarm is a SatSeconds™. The SatSeconds™ threshold value has been reduced to 25, thus providing a lower threshold to trigger a SatSeconds™ alarm. As discussed below, a simulator module may generate a SatSeconds™ alarm from the stored plethysmographic waveform data based upon simulator instructions. For example, when the stored plethysmographic waveform data generates a SatSeconds™ value breaches the 25 threshold value, the simulator module 48 may trigger an alarm.

Figure 7:
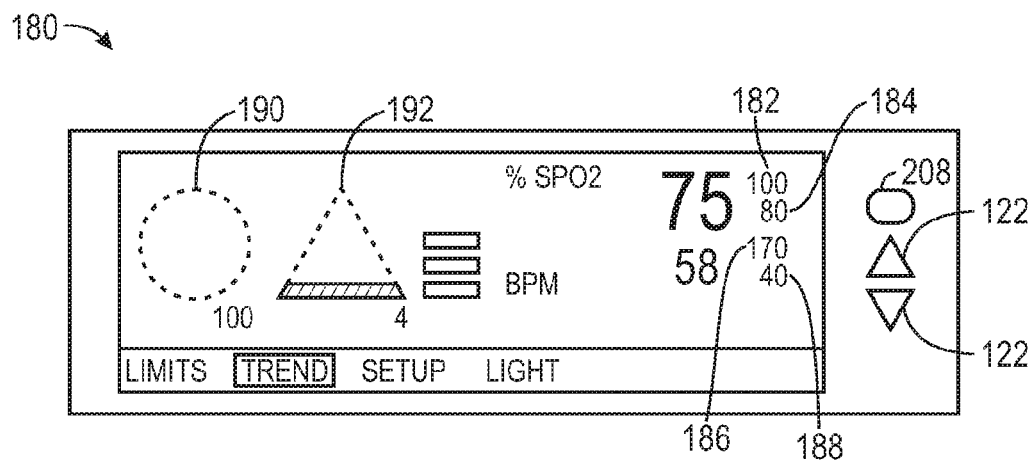
FIG. 7 illustrates a simulated display output of a medical device based upon the inputs as set forth in FIG. 4.
Figure 8:
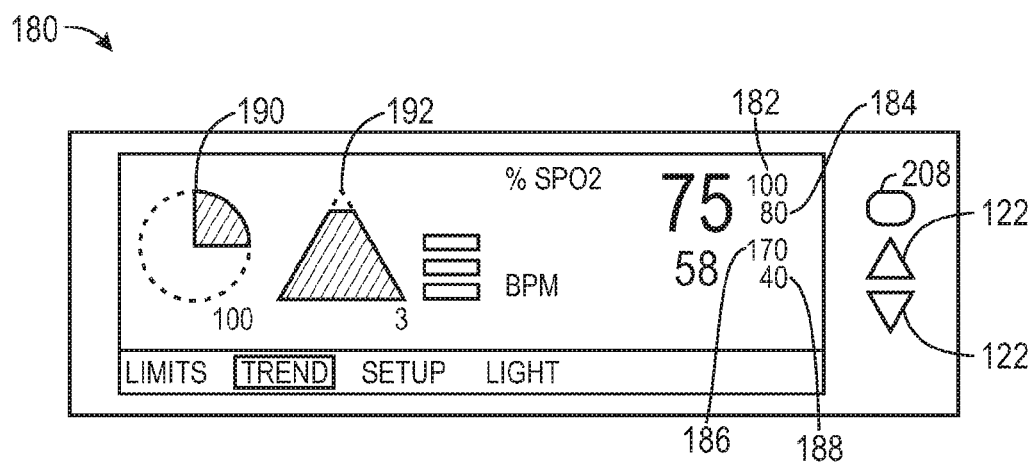
FIG. 8 illustrates a simulated display output of a medical device based upon the inputs as set forth in FIG. 5.
Figure 9:
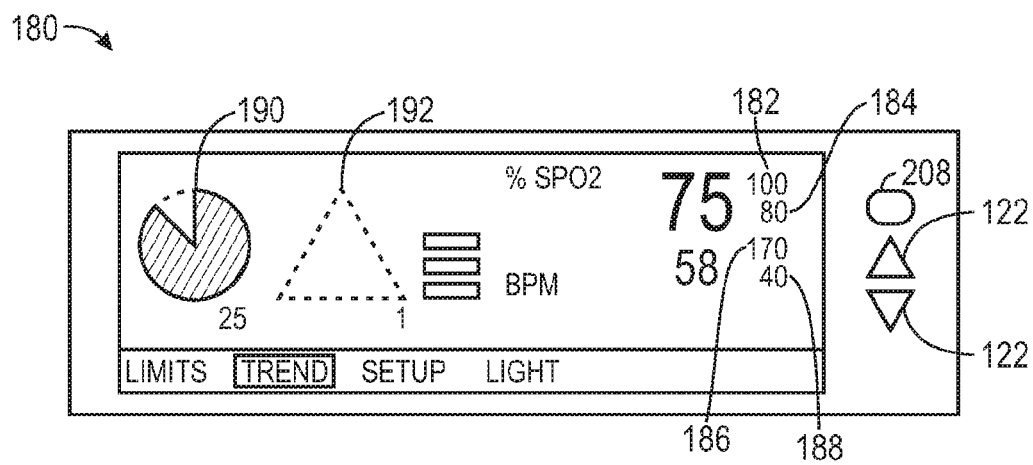
FIG. 9 illustrates a simulated display output of a medical device based upon the inputs as set forth in FIG. 6.

Based upon the inputs received from the alarm settings configuration menu 100, and the stored plethysmographic waveform data, the simulator system 10 may provide a monitor output 180 representative of an output of the medical device being simulated. For example, FIGS. 7-9 show a simulated monitor output 180 of a medical monitor with different alarm settings applied to the data. As noted, the stored data may be processed to calculate various physiological parameters, which in turn may be associated with particular alarm limits, e.g., oxygen saturation limits. For example, FIG. 7 illustrates a display output associated with alarm limits selected in FIG. 4. The upper 102 and lower 104 percentage SpO$_2$ limits as well as upper 112 and lower 114 BPM limits are displayed as upper SpO$_2$ limit 182, lower SpO$_2$ limit 184, upper BPM limit 186, and lower BPM limit 188 in the simulated monitor output 180. Additionally, the simulated monitor output 180 may provide an indication 190 of the current state of the oxygen saturation alarm and an indication 192 of the current state of the SPD alarm.

As previously discussed, the SPD settings can be adjusted to cause the SPD alarm to be more sensitive. For example, FIG. 8 shows a simulated output screen in which the SPD alarm indicator 192 is close to being triggered, based upon this increased alarm sensitivity. Here, the SPD threshold setting 110 is set to three, thus causing the sensitivity of the SPD alarm to increase The indicator 192, in the shape of a triangle, represents an indication of how close an alarm is to triggering. When the triangle is full, the alarm is triggered. The simulator module 48, through applying the SPD alarm setting to the stored plethysmographic waveform data, can simulate the display a user would observe based on the selected alarm settings to determine if the thresholds are appropriate. For example, if, upon observing the display, the simulator user 16 determines that the setting is too sensitive, the user 16 may adjust the SPD settings to a lower value, e.g., 2 or 1, and re-run the simulation.

FIG. 9 illustrates a simulated monitor output 180 in accordance with the settings of FIG. 6. Here, the SatSeconds™ setting 106 has been set to 25, which is a relatively sensitive setting. Increasing the sensitivity of the alarm, may cause the simulator module 48 to trigger the alarm more frequently when applied to the plethysmographic waveform data. Because the setting decreases the threshold for the oxygen saturation limit alarm, the alarm indicator 190, here a SatSeconds™ indicator represented by a circle, is filled more rapidly by the simulator module 48. Once the simulator module 48 determines that the alarm threshold is breached, the simulator module 48 completely fills the alarm indicator 190 and sounds an alarm representative of an alarm of the medical device being simulated.

As previously discussed, the simulator module 48 may access the stored plethysmographic waveform data from the non-volatile storage 44 or from a remote data network. The simulator module 48 then applies the alarm setting inputs, such as those received from the alarm setting configuration menu 100, to the stored plethysmographic waveform data based on instructions supplied from the simulator module 48 or from the stored plethysmographic waveform data. After applying the alarm setting inputs to the stored plethysmographic waveform data, the simulator module 48 displays the stored plethysmographic waveform data with the alarm settings applied.

Figure 10A:
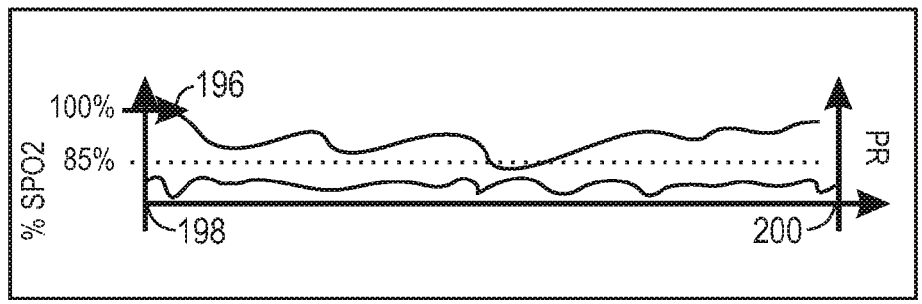
FIGS. 10A-10C depict a trend view display output progressing over time.

In certain embodiments, the simulator user 16 may select a simulated trend view representing sensor measurements of a patient over time to understand how these measurements affect the alarm systems in simulated real-time. Providing a time-based playback simulation may help the simulator user 16 to more clearly understand the alarm trigger frequency over time based upon the alarm settings provided. For example, FIGS. 10 A-C illustrate the progression of a trend view 194 over time. FIG. 10A shows the data prior to the alarm settings being applied. The time bar 196 is displayed at the starting position 198. In the depicted embodiment, alarm indicators are displayed only as they are triggered. Thus, no alarm indicators are present in FIG. 10A because simulator playback has not begun. In alternative embodiments, alarm indicators may be displayed as the alarm settings are applied to the stored plethysmographic waveform data, prior to being triggered, to provide an indication of future alarms based upon the current alarm setting inputs.

Figure 10B:
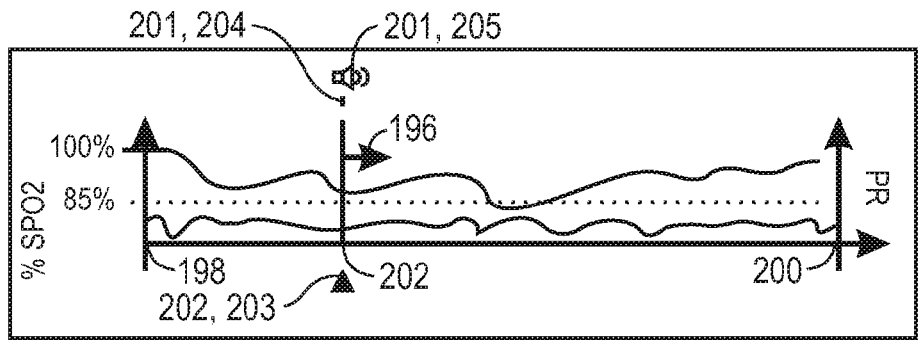

The simulator user 16 may initiate playback by selecting a play control provided by the simulator system 10. As playback commences, the time bar 196 begins to progress from the starting position 198 towards the end position 200. In the depicted embodiment, as the simulator playback progresses, simulated alarm outputs 202 are provided based upon the stored plethysmographic waveform data applied to the alarm settings inputs. For instance, the simulator module may determine that at time position 202, an SPD alarm should be triggered based upon the saturation pattern detection threshold alarm settings 110 applied to the stored plethysmographic waveform data. Thus, as depicted in FIG. 10B, an SPD alarm indicator 203 is displayed at time position 202. The alarm indicator may provide an indication of when the alarm triggered and the type of alarm that was triggered. For example, as depicted, the alarm indicator may be a shape (e.g., a triangle) which represents an alarm type. The indicator may be displayed at the time position where the alarm triggered. Additionally, in the depicted embodiment, an alarm indication bar 204 is displayed, further clarifying when the alarm occurred. In addition to the visual alarm indicators, audio alarm indicators (here, represented by a speaker icon) 205 may be employed. For example, an audio signal representative of an audio signal of the medical device being simulated may be produced through an audible alarm system 46 in the simulator system 10. The audio alarm indicators may be programmed to output an audio signal until the alarm is acknowledged by the user, or may be programmed to deactivate after a certain amount of time.

Figure 10C:
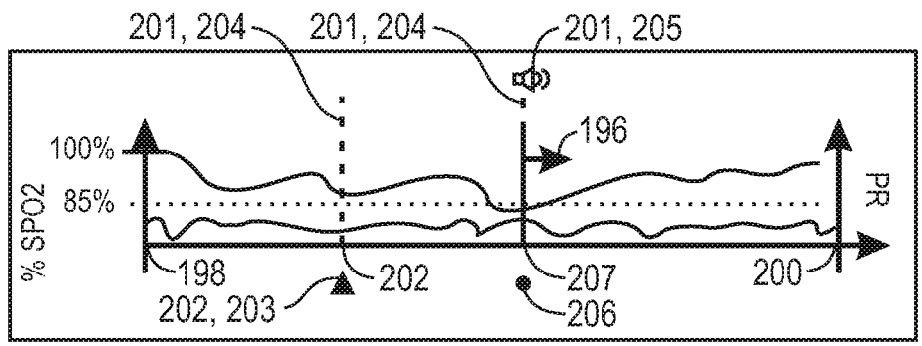

In FIG. 10C, the simulator playback is shown as having progressed towards the end position 200. At time position 207, the simulator module 48 determines that an oxygen saturation limit alarm should trigger based upon the threshold alarm settings for the oxygen saturation limit alarm 106. The simulator system 10 displays a circle symbol 206 and an alarm indication bar 204 at time position 207. Additionally, the alarm simulator system 10 provides an audible alarm indicator 205 representative of an audible alarm of the medical device being simulated. The system then continues playback, progressing towards the end position 116. The alarm indicator 205 may be deactivated through an alarm acknowledgement button 208 provided in the simulated monitor output 180, as shown in FIGS. 7-9.

Figure 11:
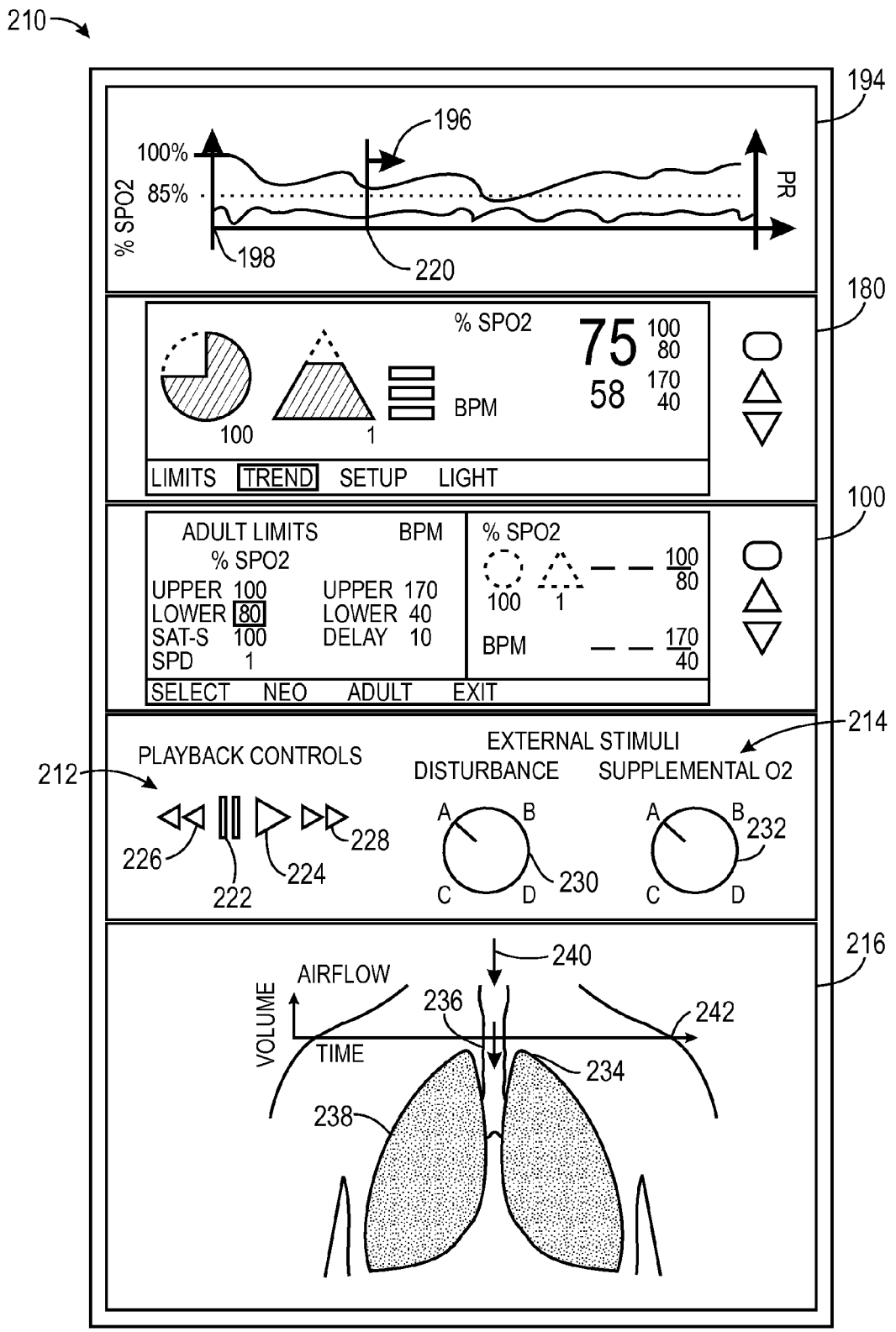
FIG. 11 is an embodiment of a simulator graphical user interface.

To demonstrate the various effects of the simulated data, the simulator system may include a multi-paneled graphical user interface 210, similar to the one depicted in FIG. 11. The graphical user interface 210 may simultaneously provide several graphical windows that may include a trend view window 194, a simulated monitor output window 180, an alarm settings configuration menu 100, playback controls 212, external stimuli controls 214, and/or a physiological illustration window 216 capable of illustrating the physiology responsible for the raw data displayed in the trend view 194. As previously discussed, the trend view window 194 may provide an illustration of a simulated patient's recorded sensor readings over time. Further, the simulated monitor output window 180 may provide a simulated graphical user interface representing a typical output for the medical device being simulated. The simulated monitor output window 180 is dynamically altered based upon the simulated sensor reading at the time position 220 where the time bar 196 is located. As previously discussed, the alarm settings configuration menu 100 may provide a graphical user interface similar to one that would be found on the simulated medical device, capable of changing the alarm settings. As the trend line changes, due to variations in the stored plethysmographic waveform data over time, the simulator system 10 may provide a simulated monitor output to the various panels based upon the current time position 220 of the simulation playback. For example, as the trend line dips below a threshold level, the simulator may provide simulated results of a SatSeconds™ indicator 190 filling. As the trend line stays under the threshold, and a calculated SatSeconds™ threshold is breached, the simulator system may sound an alarm similar to one found in the medical device being simulated. Furthermore, the simulator may illustrate that an alarm has sounded by placing an alarm indicator 201 in the trend view window 194, at the time the alarm sounded.

As the simulation time progresses, the healthcare professional or student may alter the playback rate of the simulation. For example, the user may pause the simulation or replay a portion of the simulation with either the same or different alarm configuration settings. Simulation playback may be controlled through the playback controls 212. The playback controls 212 may include a pause button 222, a play button 224, a rewind button 226, and a fast forward button 228. The user may pause playback of a running simulation using the pause button 222. Furthermore, the user may reverse playback or speedup playback using the rewind 226 and fast forward buttons 228, respectively. Additionally, the user may control playback through the trend view panel 194. The user may drag the time bar 196 in the trend view panel 194 to the location where replay is desired. For instance, if the user desires to replay the entire playback, the time bar 196 may be positioned at the start position 198 of the trend view 194. If the simulator user 16 desires to make changes to the alarm configuration or external stimuli, the user may alter these settings before or during simulation playback.

In particular embodiments, the simulator module 48 may apply simulated external stimuli to the stored plethysmographic waveform data. Such external stimuli might include motion disturbances or supplemental $O_2$. Disturbance settings may include: no disturbance, motion, arrhythmia, etc. The supplemental $O_2$ settings may simulate the effects of particular levels of supplemental $O_2$ delivered to the patient. The incorporation of these external stimuli may help the simulator user to understand the effects these inputs may have on the alarm behavior. For example, in many situations, motion may provide inaccurate sensor readings, and may trigger false alarms. Experiencing motion stimuli in the simulator system 10 may allow the simulator user 16 to become acquainted with how to accurately configure the alarms to avoid false alarms due to motion. Thus, the external stimuli controls 214 may be provided to help simulator user 16 understand how to account for these stimuli in the alarm management system. In the embodiment depicted in FIG. 11, the external stimuli controls include a disturbance knob 230 with four settings A, B, C, and D. Setting A may be assigned to a no disturbance setting that does not affect any change in the simulation when applying the disturbance settings to the stored plethysmographic waveform data. Setting B may simulate sensor reading errors caused by patient motion. In this mode, the simulator module 48 may decrease $SpO_2$ levels in the stored plethysmographic waveform data at certain time positions, to illustrate patient movement causing the sensor readings to drop. Settings C and D may simulate physiological conditions such as arrhythmia or other conditions. The simulator module 48 may alter the stored plethysmographic waveform data prior to displaying it to the simulator user 16 based on the physiological condition represented by the disturbance setting. For example, in an arrhythmia scenario, the stored plethysmographic waveform data may be modified to produce a simulated irregular heartbeat before it is presented to the simulator user 16.

The supplemental $O_2$ knob 232 provides increasing levels of supplemental $O_2$ that may be administered to the simulated patient. Setting A may represent no supplemental $O_2$ being administered to a patient, while settings B, C, and D provide increasing levels of supplemental $O_2$. As the supplemental $O_2$ levels are increased, the simulator module 48 may increase the $O_2$ readings displayed in the trend view 194. As the supplemental $O_2$ levels are reduced, the simulator module 48 may reduce the $O_2$ readings displayed in the trend view 194.

In an effort to more clearly demonstrate the physiological condition associated with a particular data set, the simulator system 10 may include additional clinical information, depicted here in the form of a physiological illustration window 216. The physiological illustration window 216 may provide an anatomical representation 234 of the physiology causing the displayed trend view 194. For example, a simulator system 10 may simulate an airway obstruction. The simulator system 10 will import stored plethysmographic waveform data for the airway obstruction physiological condition. Based on the stored plethysmographic waveform data, the trend view 194 may be derived and displayed. The physiological illustration panel may display the relevant anatomy for the physiological condition, here a trachea 236 and lungs 238. The physiological illustration window may further provide relevant physiological information of the anatomy through animation 240 or charts 242. For example, in the depicted embodiment, the airflow volume over time, illustrated in the chart 242, may take into account patient airway obstruction.

In addition, the simulator system 10 may include a user assessment module 50 designed to assess a user's understanding of the alarm settings of the medical device under specific conditions for clinical education and documentation purposes. When clinical scenarios are incorporated, the user assessment module 50 may provide training on the evolution, presentation, and response to therapy of various situations that result in hypoxemia. The user assessment module 50 may provide an interactive graphical user interface with a preset library of questions and prompts designed to guide the user through analysis, diagnosis, and possible interventions. As the user answers these questions, the simulator system 10 may immediately respond by providing outputs in line with the possible effects of the user's selections.

Figure 12:
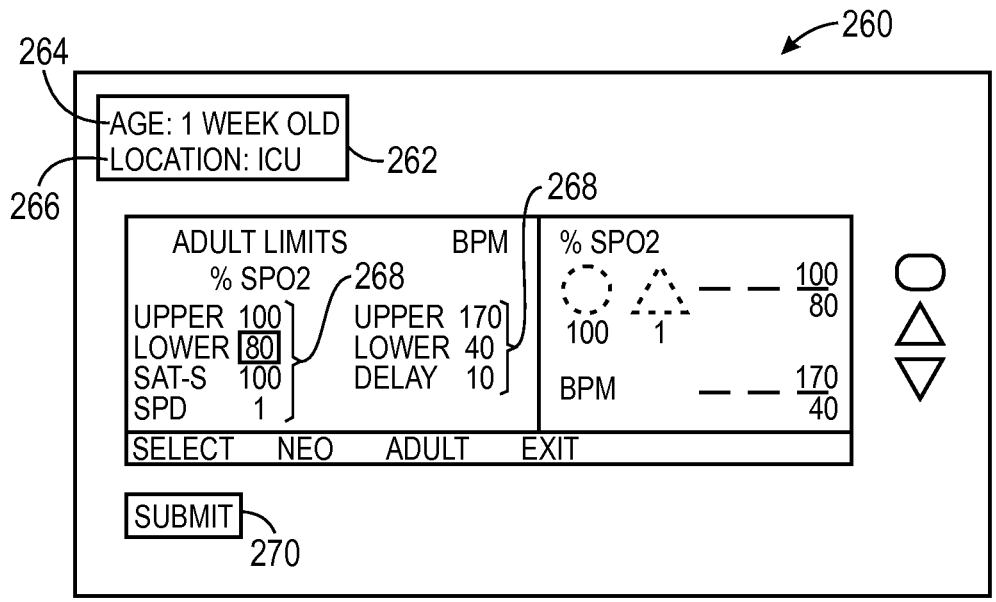
FIG. 12 depicts a user assessment module output that allows a user to input alarm settings based upon specific patient information.
Figure 13:
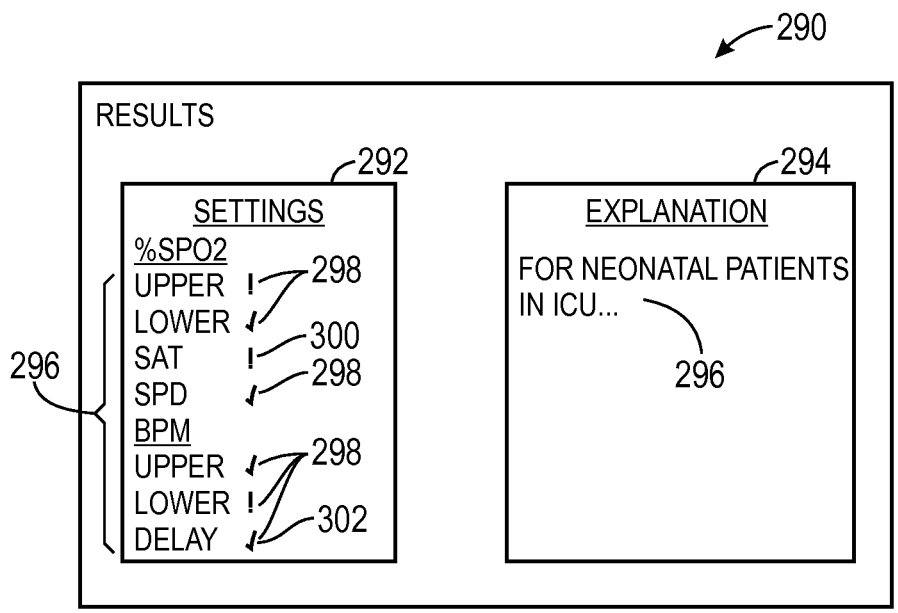
FIG. 13 is an illustration of a results output screen derived from the user interaction with the user assessment module output of FIG. 12.

In one embodiment, illustrated in FIG. 12, the user assessment module 50 provides a user with a training input screen 260 via the display 12 of the simulator system 10. The training input screen 260 includes patient and/or medical treatment characteristics box 262, providing characteristics such as the age of a patient 264, the treatment location of the patient 266, and/or the suspected physiological condition of the patient. The patient characteristics as well as evaluation rules for the user assessment module 50 may be obtained through training data stored on local non-volatile storage 44 or through data obtained from a remote network. The simulator user 16 may input alarm settings 268 based upon the provided patient and/or medical treatment characteristics provided in the characteristics box 262. After the user is done configuring the alarms based upon the characteristic data, the user may then submit the alarm settings configuration for review by the user assessment module 50. In the depicted embodiment, the submission occurs upon selecting a "submit" button 270 provided in the training input screen 260. Upon receiving the submitted alarm configuration settings 268, the user assessment module 50 evaluates the configuration settings 268 based upon the characteristic data provided in the characteristics box 262 and the evaluation rules obtained by the user assessment module 50. As illustrated in FIG. 13, the user assessment module 50 may provide a results screen 290 illustrating the appropriateness of the alarm setting based on the alarm configuration settings 268 applied to the characteristics in the characteristics box 262. In the depicted embodiment, the results screen 290 provides a settings analysis window 292 and an explanation window 294. The settings analysis window 292 provides a list 296 of each of the alarm settings. Each alarm setting includes an indicator 298 illustrating the appropriateness of the alarm setting. In the depicted embodiment, an exclamation mark indicator 300 illustrates a possible inappropriate alarm setting. A check mark indicator 302 illustrates an appropriate alarm setting. The simulator user 16 is provided an explanation 296 of the appropriateness of the alarm setting in the explanation box 294. For example, in FIG. 12 the patient characteristics provided that the patient was neonatal. The user assessment module 50 may include evaluation instructions suggesting that the upper $SpO_2$ limit should be less than 100% for neonatal patients, e.g., to warn of lung overinflation. Thus, the simulator user 16 is provided an exclamation mark indicator 300 on the upper $SpO_2$ setting in the settings analysis window 292. Further, the user assessment module 50 provides an explanation of a desired neonatal overinflation warning in the explanation box 294.

Figure 14:
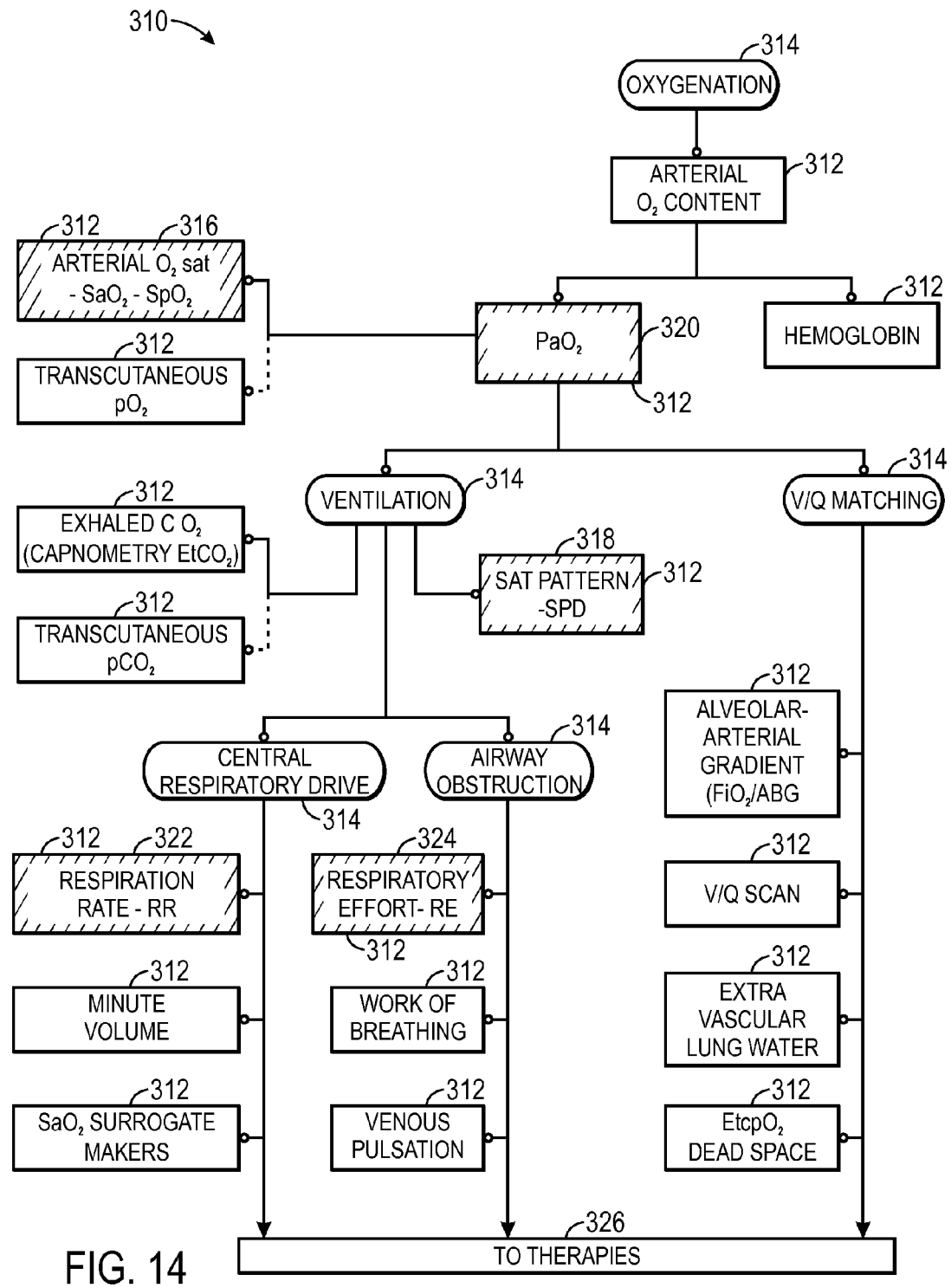
FIG. 14 is an embodiment of a clinical decision tree provided by the user assessment module of the simulator system.

For further instruction, the user assessment module may include a graphical clinical decision tree 310, as depicted in FIG. 14. The decision tree 310 may include parameters 312 and physiological conditions to be measured 314. The parameters 312 and physiological conditions 314 may be denoted by different shapes in the decision tree 310. For example, parameters 312 may be displayed in a rectangular shape while physiological conditions 314 are displayed in an oval shape. The user assessment module 50 may provide parameters that are outside of normal threshold limits. The decision tree 310 may include highlighted parameters, illustrating that these parameters are outside the normal threshold limits. Providing the decision tree 310 with highlighted parameters and/or physiological conditions may assist a simulator user 16 in stepping through a diagnosis associated with the underlying physiological condition. For example, in the depicted decision tree 310, the Arterial $O_2$ parameter 316, the Saturation Pattern parameter 318, the Partial Pressure ($PaO_2$) parameter 320, the Respiration Rate parameter 322, and the Respiratory Effort parameter 324 are highlighted. These highlighted parameters may direct the user to the proper physiological conditions 314 and the potential therapies 326.

While the disclosure may be susceptible to various modifications and alternative forms, specific embodiments have been shown by way of example in the drawings and will be described in detail herein. However, it should be understood that the disclosure is not intended to be limited to the particular forms disclosed. Rather, the disclosure is to cover all modifications, equivalents and alternatives falling within the spirit and scope of the disclosure as defined by the following appended claims.

What is claimed is:

1. A method comprising the steps of:
  receiving an input related to an alarm setting;
  accessing stored plethysmographic waveform data, wherein the stored plethysmographic waveform data is representative of data obtained by a medical device;
  applying the alarm setting to the plethysmographic waveform data;
  displaying a simulated output for the medical device based on the plethysmographic waveform data with the alarm setting applied; and
  providing a simulated alarm output representative of an actual alarm output of the medical device based upon the alarm setting and the plethysmographic waveform data.

2. The method of claim 1, comprising displaying the plethysmographic waveform data comprises a trend view.

3. The method of claim 1, wherein the medical device comprises a pulse oximetry monitor.

4. The method of claim 1, comprising displaying information related to a clinical condition of a patient, wherein the stored plethysmographic waveform data is representative of data obtained from a patient with the clinical condition.

5. The method of claim 1, comprising receiving a second input related to a playback time for the displayed plethysmographic waveform data.

6. The method of claim 5, where the playback is representative of real-time.

7. The method of claim 1, comprising receiving a second input related to motion, arrhythmia, or a level of supplemental oxygen and applying the second input to the data.

8. The method of claim 1, wherein the simulated alarm output comprises a visual alarm indicator, an audible alarm indicator, or a combination thereof.

9. The method of claim 1, comprising:
receiving a second user input related to a second alarm setting;
applying the second alarm setting to the plethysmographic waveform data;
displaying a simulated output for the medical device based on the plethysmographic waveform data with the second alarm setting applied; and
providing a simulated alarm output representative of an actual alarm output of the medical device based upon the second alarm setting and the plethysmographic waveform data.

10. The method of claim 9, wherein the first alarm setting and the second alarm setting relate to the same alarm type.

11. The method of claim 10, wherein the first alarm setting and the second alarm setting relate to a saturation pattern detection alarm or an oxygen saturation limit alarm.

12. The method of claim 10, comprising displaying the simulated output for the medical device with the first alarm setting applied adjacent to the simulated output for the medical device with the second alarm setting applied.

13. The method of claim 9, wherein the first alarm setting and the second alarm setting relate to different alarm types.

14. The method of claim 13, wherein the first alarm setting relates to a saturation pattern detection alarm and the second alarm setting relates to an oxygen saturation limit alarm.

15. A system comprising:
a memory storing plethysmographic waveform data representative of data obtained by a medical device;
a processor configured to execute instructions for:
receiving an input related to an alarm setting from the alarm settings configuration menu;
accessing the stored plethysmographic waveform data from the memory;
applying the alarm setting to the plethysmographic waveform data using alarm algorithms employed in the medical device; and
providing a simulated alarm output representative of an actual alarm output of the medical device; and
a display configured to display the simulated alarm output.

16. The system of claim 15, wherein the processor is configured to receive a second input related to motion, arrhythmia, or a level of supplemental oxygen and to apply the input to the data.

17. The system of claim 15, wherein the processor is configured to provide clinical information based on the plethysmographic waveform data.

18. The system of claim 15, wherein the simulated alarm output comprises a graphical indicator.

19. The system of claim 18, wherein the graphical indicator comprises a triangular indicator that fills when the simulated alarm output comprises triggering events beyond a threshold.

20. A tangible, machine-readable medium having instructions encoded thereon for execution by a processor, comprising:
instructions for receiving an input related to an alarm setting;
instructions for accessing stored plethysmographic waveform data, wherein the stored plethysmographic waveform data is representative of data obtained by a medical device;
instructions for applying the alarm setting to the plethysmographic waveform data; and
instructions for displaying a simulated output for the medical device based on the plethysmographic waveform data with the alarm setting applied.

* * * * *